United States Patent [19]

Mount et al.

[11] 4,149,992

[45] Apr. 17, 1979

[54] METHOD FOR PREPARING AN OXIDATION CATALYST

[75] Inventors: Ramon A. Mount; Harold Raffelson; Warn D. Robinson, all of St. Louis, Mo.

[73] Assignee: Monsanto Company, St. Louis, Mo.

[21] Appl. No.: 698,390

[22] Filed: Jun. 21, 1976

Related U.S. Application Data

[62] Division of Ser. No. 552,481, Feb. 24, 1975, abandoned.

[51] Int. Cl.$^2$ .......................... B01J 27/14; B01J 31/02
[52] U.S. Cl. .................................. 252/435; 252/437; 252/430
[58] Field of Search ..................... 252/435, 437, 430

[56] References Cited

U.S. PATENT DOCUMENTS

| | | | |
|---|---|---|---|
| 2,643,231 | 6/1953 | Erickson | 252/448 |
| 2,875,159 | 2/1959 | Erickson | 252/448 |
| 3,060,132 | 10/1962 | Weeks et al. | 252/429 B |
| 3,474,041 | 10/1969 | Kerr | 252/437 X |
| 3,657,151 | 4/1972 | Noble | 252/453 X |
| 3,789,018 | 1/1974 | Levy et al. | 252/430 X |
| 3,893,943 | 7/1975 | Willard, Sr. | 252/452 X |
| 3,907,707 | 9/1975 | Raffelson et al. | 252/437 |

*Primary Examiner*—Delbert E. Gantz
*Assistant Examiner*—William G. Wright
*Attorney, Agent, or Firm*—James C. Logomasini; Paul L. Passley; Stanley M. Tarter

[57] ABSTRACT

In a method for preparing a phosphorus-vanadium-oxygen catalyst wherein a pentavalent vanadium compound and a trivalent phosphorus compound are brought together in a liquid reaction zone under conditions to provide a substantial amount of tetravalent vanadium and to form a phosphorus-vanadium-oxygen catalyst precursor having a phosphorus to vanadium atom ratio between about 0.9:1 and about 2:1, the improvement of this invention comprises adding a sufficient amount of a surfactant to the liquid reaction zone to form a dispersion which comprises a liquid, the surfactant and a dispersoid of the phosphorus-vanadium-oxygen catalyst precursor.

7 Claims, No Drawings

METHOD FOR PREPARING AN OXIDATION CATALYST

This is a division of application Ser. No. 552,481, now abandoned, filed Feb. 24, 1975.

BACKGROUND OF THE INVENTION

This invention relates to a method for preparing catalysts useful in the manufacture of dicarboxylic acid anhydrides by the oxidation of hydrocarbons. More particularly, it is directed to a method for the preparation of catalysts suitable for producing maleic anhydride from saturated hydrocarbons.

Maleic anhydride is of significant commercial interest throughout the world. It is used alone or in combination with other acids in the manufacture of alkyd and polyester resins. It is also a versatile intermedite for chemical synthesis. Significant quantities of maleic anhydride are produced each year to satisfy these needs.

The prior art teaches that vanadium catalysts are well suited to the production of maleic anhydride from hydrocarbons, and the prior art further teaches that phosphorus-vanadium-oxygen catalysts can be prepared in a number of ways. For example, these catalysts can be prepared by precipitating the vanadium and phosphorus compounds either with or without a carrier from a colloidal dispersion of the ingredients in an inert liquid, and thereafter calcining the precipitate. Catalysts can also be prepared by dissolving vanadium and phosphorus compound in a common solvent and thereafter depositing the resulting phosphorus-vanadium-oxygen compound from solution on a carrier.

Many prior art procedures for the preparation of vanadium catalysts teach that it is preferable to reduce the vanadium in solution to the tetravalent state. Hence, the prior art teaches that vanadium compounds can be contacted with a reducing acid, such as hydrochloric acid or oxalic acid, and then heated until the vanadium is reduced to a valence state of less than five before the compounds are subsequently recovered and used as catalysts.

Although the prior art procedures provide acceptable catalysts, there are attendant processing difficulties with such procedures. It has been discovered that phosphorus-vanadium-oxygen catalyst precursors can be prepared rapidly by reacting a trivalent phosphorus compound with a vanadium compound to provide tetravalent vanadium using elevated temperatures and pressures, such as are found in an autoclave. Although such procedures usually provide a finely divided solid catalyst precursor, from time to time the procedure forms large crystals of the precursor; upon forming a catalyst from such a precursor, low yields of maleic anhydride are obtained. These and other disadvantages are overcome by the present method for preparing phosphorus-vanadium-oxygen catalysts to consistently provide finely divided precursors that are converted to catalysts to provide high yields of maleic anhydride.

SUMMARY OF THE INVENTION

It is an object of this invention to provide an improved process for preparing catalysts. It is another object to provide an improved process for preparing phosphorus-vanadium-oxygen catalysts suitable for converting saturated hydrocarbons to maleic anhydride. It is another object to provide an improved process for preparing phosphorus-vanadium-oxygen catalysts particularly suitable for converting butane to maleic anhydride.

These and other objects are achieved by the improved method described herein for preparing a phosphorus-vanadium-oxygen catalyst wherein a pentavalent vanadium compound and a trivalent phosphorus compound are brought together in a liquid reaction zone under conditions to provide a substantial amount of tetravalent vanadium and to form a phosphorus-vanadium-oxygen precursor having a phosphorus to vanadium atom ratio of from about 0.9:1 to about 2:1, the improvement which comprises adding a sufficient amount of a surfactant to the liquid reaction zone to form a finely divided phosphorus-vanadium-oxygen catalyst precursor.

Broadly described, the catalysts of this invention are prepared by contacting a pentavalent vanadium compound with a trivalent phosphorus compound in a liquid medium containing a surfactant to provide a catalyst precursor containing a substantial amount of tetravalent vanadium. The precursor is formed into structures for use in a maleic anhydride reactor and the structures are calcined to form the catalysts of this invention.

For the purposes of this invention, the term "catalytic activity" means the ability of a catalyst to convert a particular feed stock such as butane at a particular temperature to other compounds. The term "selectivity" means the ratio of the moles of maleic anhydride obtained to the moles of hydrocarbon reacted. The term "yield" means the ratio of the moles of maleic anhydride obtained to the moles of hydrocarbon introduced into the reaction. The term "space velocity" means the hourly volume of gaseous feed expressed in cubic centimeters (cc) at 60° F. and standard atmospheric pressure divided by the catalyst bulk volume expressed in cubic centimeters (cc), the term being expressed as cc/cc/hour.

The vanadium compounds useful as a source of vanadium in the catalyst precursors are those known to the art to be useful for preparing catalysts to oxidize hydrocarbons. Suitable vanadium compounds include: vanadium oxides such as vanadium pentoxide and the like; vanadium oxyhalides such as vanadyl trichloride, vanadyl tribromide and the like; vanadium-containing acids such as metavanadic acid, pyrovanadic acid, and the like; vanadium salts such as ammonium metavanadate, vanadium sulfate, vanadium phosphate, vanadyl formate, vanadyl oxalate and the like. However, vanadium pentoxide is preferred.

The trivalent phosphorus compounds useful to provide a substantial amount of tetravalent vanadium in the catalyst precursors are also those known to the art. Suitable trivalent phosphorus compounds include: phosphorus acids such as orthophosphorous acid, pyrophosphorous acid, metaphosphorous acid, hypophosphorous acid and the like; phosphorus trihalides such as phosphorus tribromide, phosphorus trichloride, phosphorus triiodide and the like; trivalent phosphorus oxides such as phosphorus trioxide and the like; organic phosphites, i.e., compounds of the type $P(OR)_3$ where R is an aryl or alkyl group such as trimethyl phosphite, triethyl phosphite, tripropyl phosphite, ethyl propyl phosphite and the like. However, phosphorous acids, such as orthophosphorous acid, are preferred.

As an additional source of phosphorus in the catalyst precursors, pentavalent phosphorus compounds known to the art to be useful for preparing catalysts to oxidize hydrocarbons to maleic anhydride can be used. While trivalent phosphorus compounds can be used as the only source of phosphorus, pentavalent phosphorus compounds can be used as an additional source of phosphorus and their use with the trivalent phosphorus compounds is preferred. Suitable pentavalent phosphorus compounds include: phosphoric acids such as metaphosphoric acid, orthophosphoric acid, triphosphoric acid, pyrophosphoric acid and the like; phosphorus oxides such as phosphorus pentoxide and the like; phosphorus halides such as phosphorus oxyiodide, phosphorus pentachloride, phosphorus oxybromide and the like; and organophosphorus compounds such as ethyl phosphate, methyl phosphate and the like. However, phosphoric acids, such as orthophosphoric acid and phosphorus pentoxide are preferred.

The surfactants which can be used within the compositions of this invention include anionic, nonionic, zwitter-ionic, ampholytic compounds and mixtures thereof. These suitable substances are outlined at length below.

(a) Anionic surfactants which can be used in the compositions of this invention include both soap and non-soap compounds. Examples of suitable soaps are the sodium, potassium, ammonium and alkylolammonium salts of higher fatty acids ($C_{10}$–$C_{20}$). Particularly useful are the sodium or potassium salts of the mixtures of fatty acids derived from coconut oil and tallow, i.e., sodium or potassium tallow and coconut soap. Examples of anionic organic non-soap compounds are the water soluble salts, alkali metal salts, of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals). Important examples of the synthetic surfactants which form a part of the compositions of the present invention are the sodium or potassium alkyl sulfates, especially those obtained by sulfating the higher alcohols ($C_8$–$C_{18}$ carbon atoms) produced by reducing the glycerides of tallow or coconut oil; sodium or potassium alkyl benzenesulfonates, such as are described in U.S. Pat. Nos. 2,220,009 and 2,477,383 in which the alkyl group contains from about 9 to about 15 carbon atoms; other examples of alkali metal alkylbenzene sulfonates are those in which the alkyl radical is a straight chain aliphatic radical containing from about 10 to about 20 carbon atoms for instance, 2-phenyl-dodecane sulfonate and 3-phenyl-dodecanesulfonate; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about 1 to 6 moles of ethylene oxide; sodium or potassium salts of alkylphenol ethylene oxide ether sulfate with about 1 to about 10 units of ethylene oxide per molecule end in which the alkyl radicals contain about 9 to about 12 carbon atoms; the reaction product of fatty acids esterified with isothionic acid and neutralized with sodium hydroxide where, for example, the fatty acids are derived from coconut oil; sodium or potassium salts of fatty acid amide of a methyl tauride in which the fatty acids, for example, are derived from coconut oil; and others known in the art, a number being specifically set forth in U.S. Pat. Nos. 2,486,921, 2,486,922 and 2,396,278.

(b) Nonionic surfactants may be broadly defined as compounds aliphatic or alkylaromatic in nature which do not ionize in water solution. For example, a well known class of nonionic surfactants is made available on the market under the trade name of "Pluronic." These compounds are formed by condensing ethylene oxide with a hydrophobic base formed by the condensation of propylene oxide with propylene glycol. The hydrophobic portion of the molecule which, of course, exhibits water insolubility has a molecular weight of from about 1,500 to 1,800. The addition of polyoxyethylene radicals to this hydrophobic portion tends to increase the water solubility of the molecule as a whole and the liquid character of the product is retained up to the point where polyoxyethylene content is about 50% of the total weight of the condensation product.

Other suitable surfactants include:

(1) The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 25 moles of ethylene oxide per mole of alkyl phenol. The alkyl substituent in such compounds may be derived from polymerized propylene, diisobutylene, octene, or nonene, for example.

(2) Those derived from the condensation of ethylene oxide with the product resulting from the reaction of propylene oxide and ethylenediamine. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said hydrophobic base having a molecular weight of the order of 2,500 to 3,000 are satisfactory.

(3) The condensation product of aliphatic alcohols having from 8 to 18 carbon atoms, in either straight chain or branched chain configuration, with ethylene oxide, e.g., a coconut alcohol-ethylene oxide condensate having from 10 to 30 moles of ethylene oxide per mole of coconut alcohol, the coconut alcohol fraction having from 10 to 14 carbon atoms.

(4) Long chain tertiary amine oxides corresponding to the following general formula, $R_1R_2R_3N \rightarrow O$, wherein $R_1$ is an alkyl radical of from about 8 to 18 carbon atoms, and $R_2$ and $R_3$ are each methyl or ethyl radicals. The arrow in the formula is a conventional repesentation of a semipolar bond. Examples of amine oxides suitable for use in this invention include dimethyldodecylamine oxide, dimethyloctylamine oxide, dimethyldecylamine oxide, dimethyltetradecylamine oxide, dimethylhexadecylamine oxide.

(5) Long chain tertiary phosphine oxides corresponding to the following formula $RR'R''P \rightarrow O$, wherein R is an alkyl, alkenyl or monohydroxyalkyl radical ranging from 10 to 18 carbon atoms in chain length and R' and R" are each alkyl or monohydroxyalkyl groups containing from 1 to 3 carbon atoms. The arrow in the formula is a conventional representation of a semi-polar bond. Examples of suitable phosphine oxides are:

dimethyldodecylphosphine oxide,
dimethyltetradecylphosphine oxide,
ethylmethyltetradecylphosphine oxide,
cetyldimethylphosphine oxide,
dimethylstearylphosphine oxide, cetylethylpropylphosphine oxide,
diethyldodecylphosphine oxide,
diethyltetradecylphosphine, oxide
bis(hydroxymethyl)dodecylphosphine oxide,
bis(2-hydroxyethyl)dodecylphosphine oxide,
2-hydroxypropylmethyltetradecylphosphine oxide,
dimethyloleylphosphine oxide, and
dimethyl-2-hydroxydodecylphosphine oxide.

(6) Dialkyl sulfoxides corresponding to the following formula, RR'S→O, wherein R is an alkyl, alkenyl, beta- or gamma-monohydroxyalkyl radical or an alkyl or beta- or gamma-monohydroxyalkyl radical containing one or two other oxygen atoms in the chain, the R groups ranging from 10 to 18 carbon atoms in chain length, and wherein R' is methyl or ethyl. Examples of suitable sulfoxide compounds are:
dodecyl methyl sulfoxide
tetradecyl methyl sulfoxide
3-hydroxytridecyl methyl sulfoxide
2-hydroxydodecyl methyl sulfoxide
3-hydroxy-4-decoxybutyl methyl sulfoxide
3-hydroxy-4-dodecoxybutyl methyl sulfoxide
2-hydroxy-3-decoxypropyl methyl sulfoxide
2-hydroxy-3-dodecoxypropyl methyl sulfoxide
dodecyl ethyl sulfoxide
2-hydroxydodecyl ethyl sulfoxide (c) Ampholytic synthetic surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group. Examples of compounds falling within this definition are sodium-3-dodecylaminopropionate and sodium-3-dodecylaminopropanesulfonate.

(d) Zwitterionic synthetic surfactants can be broadly described as derivatives of aliphatic quarternary ammonium compounds in which the aliphatic radical may be straight chain or branched and wherein one of the aliphatic substituents contains from about 8 to 18 carbon atoms and one contains an anionic water solubilizing group. Examples of compounds falling within this definition are 3-(N,N-dimethyl-N-hexadecylammonio)propane-1-sulfonate and 3-(N,N-dimethyl-N-hexadecylammonio)-2-hydroxypropane-1-sulfonate.

The anionic, nonionic, ampholytic and zwitterionic synthetic surfactants mentioned above can be used singly or in combination in the practice of the present invention. The above examples are merely specific illustrations of the numerous surfactants which can find application within the scope of this invention. Nonionic surfactants are generally preferred, and nonylphenol reacted with 9 moles ethylene oxide is especially preferred.

By the process of the present invention, a pentavalent vanadium compound is brought together with a trivalent phosphorus compounds in a liquid reaction zone. The liquids suitable for use in the reaction zone in the process of the present invention are those known to the art to be useful for preparing phosphorus-vanadium-oxygen catalysts. Suitable liquids include: lower molecular weight organic compounds such as alcohols, like methanol, ethanol, propanol, butanol, isobutanol, and the like; ketones such as methyl ketone, methylethyl ketone, and the like; ethers such as ethyl ether, dioxane and the like. Aromatic compounds such as benzene, toluene, benzyl chloride and the like are also useful. Since it is only necessary that the liquid be chemically inert with the precursor under the conditions that the catalyst precursor is formed, and that the catalyst precursor is somewhat insoluble in the liquid, water can be used as the liquid in the process of the present invention, and its use is preferred.

The amount of liquid is not critical, as will occur to those skilled in the art, provided that there is sufficient liquid to permit the formation of a phosphorus-vanadium-oxygen precursor under conditions to provide a substantial amount of tetravalent vanadium. As little as 50 weight percent liquid, based on the weight of the phosphorus compound and the vanadium compound, is effective in the method of the present invention. There is no theoretical upper limit to the amount of liquid that can be used, but excessive amounts of liquid are not beneficial and require handling large volumes of material unnecessarily. It is preferred to use a weight ratio of liquid to phosphorus and vanadium compounds between about 1:2 and about 2:1.

The amount of surfactant for use in the process of the present invention can vary within wide limits. It has been found that the amount of surfactant should be at least about 0.01 weight percent, based on the weight of the phosphorus compound, the vanadium compound and the liquid, since at lower concentrations the effect of the surfactant in the method of the present invention is not seen. Although there is no upper limit as to the amount of surfactant that can be used, there does not seem to be an advantage to using more than about 0.5 weight percent based on the weight of the liquid, the phosphorus compound and the vanadium compound. It is preferred to use between about 0.05 and about 0.2 weight percent surfactant, based on the weight of the liquid, the phosphorus compound and the vanadium compound.

The atom ratio of phosphorus to vanadium in the precursor is important since it controls the phosphorus to vanadium atom ratio in the final catalyst. When phosphorus-vanadium-oxygen precursors contain a phosphorus to vanadium atom ratio below about 0.9:1 or above about 2:1, the benefits of the present invention are not achieved since the yield of maleic anhydride using the catalyst prepared from these precursors is low. It is preferred that phosphorus-vanadium-oxygen precursors have a phosphorus to vanadium atom ratio in the range of about 1:1 to about 1.5:1. When the catalyst is used to convert a feed that is primarily butane to maleic anhydride, it is even more preferable that the precursor have a phosphorus to vanadium atom ratio of about 1:1 to about 1.2:1, say about 1.1:1.

To prepare the catalyst precursors by the process of the present invention, a predetermined amount of vanadium compound in which the vanadium is in the pentavalent state is brought together with stirring with a sufficient amount of trivalent phosphorus compound in a liquid reaction zone containing the surfactant to provide a substantial amount, i.e., at least 50 atom percent, of tetravalent vanadium. It is preferable to use a stoichiometric amount of trivalent phosphorus compound to provide the tetravalent vanadium, and even more preferable to use an excess of the stoichiometric amount of trivalent phosphorus compound to insure that substantially all the vanadium is in the tetravalent state. It is preferred to use phosphorus acid as the trivalent phosphorus compound which provides an acid medium to form the precursor and provides the tetravalent vanadium. The liquid containing the trivalent phosphorus compound and the vanadium compound is heated until a blue solution is obtained, indicating that a substantial amount of the vanadium is in the tetravalent state. The amount of time required to dissolve the phosphorus and vanadium compounds and to provide a substantial amount of the vanadium in the tetravalent state to form the catalyst precursors varies from batch to batch, depending upon the compounds used as starting materials and the temperature at which the compounds are heated. However, as will occur to those skilled in the art, an aliquot of the solution can be analyzed to insure that a major part of the vanadium is in the tetravalent state. In general, however, heating the solution to at least 100° C. for up to about 4 hours is sufficient.

The surfactant can be added to the reaction zone by the method of the present invention at any number of steps during the preparation of the catalyst. The surfactant can be added to the reaction zone prior to the time the phosphorus compound and the vanadium compound are brought together in the reaction zone. On the other hand, the surfactant can be added to the reaction zone after the phosphorus compound and the vanadium compound are brought together in the reaction zone, or even after the formation of the precursor. For example, it has been found that if the phosphorus compound and the vanadium compound ae brought together under conditions that large crystals are formed, the surfactant can be added to the reaction zone under heat and agitation to form the precursor of the present invention. However, it is preferred to add the surfactant to the reaction zone when the phosphorus compound and the vanadium compound are brought together in the reaction zone. Regardless of when the surfactant is added, a dispersion is obtained which comprises a liquid and at least about 0.01 weight percent of a surfactant, based on the total weight of the dispersion, and a dispersoid which comprises a phosphorus-vanadium-oxygen precursor having a phosphorus to vanadium atom ratio between about 0.9:1 and about 2:1, wherein a substantial amount of the vanadium is tetravalent vanadium.

In the preferred method of making the catalysts of this invention, a pentavalent vanadium compound, such as vanadium pentoxide, is contacted in water with a mixture of phosphorus acid and phosphoric acid in such amounts that the phosphorus to vanadium atom ratio is about 1.1:1. The aqueous acid mixture should contain, in addition to the surfactant, phosphorus acid in excess of the stoichiometric amount required to reduce all the vanadium to tetravalent vanadium. The mixture of phosphorus and vanadium compounds is then heated to form a phosphorus-vanadium-oxygen precursor. Heating at 100° C. for as long as 24 hours may be required to provide tetravalent vanadium and form the precursor, but the heating time can be shortened substantially by heating the mixture up to as high as 500° C. at superatomospheric pressures. It is preferred to place the mixture of phosphorus and vanadium compounds in a closed system at room temperature, and then heat the mixture to about 150° C. in the closed system such as a stirred autoclave for about 3 hours. The phosphorus-vanadium-oxygen precursors are recovered and converted to catalysts by methods known to the art. For example, the precursors can be deposited on a carrier, such as alumina or titania, or the precursors can be dried by gentle heating to provide solid phosphorus-vanadium-oxygen precursors. On the other hand, the solid precursors can be filtered from the liquid by methods known to the art. After the phosphorus-vanadium-oxygen precursors are recovered, they are then formed into structures suitable for use in a maleic anhydride reactor. Techniques for forming appropriate structures from precursors for use in a fluidized bed reactor or in a fixed tube heat exchanger type reactor are well-known to those skilled in the art. For example, the precursors can be structured for use in a fluidized bed reactor by depositing the phosphorus-vanadium-oxygen precursors on a carrier. Alternatively, dried precursors can be comminuted for use in a fluidized bed reactor. On the other hand, precursors can be structured for use in a fixed tube reactor by prilling or tabletting the precursors. After the phosphorus-vanadium-oxygen precursors are formed into the structures which will be used in a maleic anhydride reactor, the precursors are then calcined at temperatures between about 350° C. and about 600° C. for at least about 2 hours to provide the catalysts of the present invention.

After the phosphorus-vanadium-oxygen precursor has been calcined, the catalyst thus formed is placed in a reactor used to convert hydrocarbons to maleic anhydride. Thereafter, a hydrocarbon and air mixture can be passed through the catalyst at temperatures between about 350° C. and 600° C. at concentrations of from about 1 to about 10 mole percent hydrocarbon at a space velocity up to 3000 cc/cc/hour to produce maleic anhydride.

However, as is well-known in the art, the initial yield of maleic anhydride may be low, and if this is the case, the catalyst can be "conditioned" by passing low concentrations of hydrocarbon in air at low space velocities through the catalyst for a period of time before production operations begin.

The catalysts of the present invention are useful in a variety of reactors to convert hydrocarbons to maleic anhydride. Both fluidized bed reactors and fixed tube heat exchanger type reactors are satisfactory and the details of the operation of such reactors are well known to those skilled in the art. The reaction to convert hydrocarbons to maleic anhydride requires only passing the hydrocarbons admixed with a free oxygen-containing gas, such as air or oxygen enriched air, through the catalyst at elevated temperatures. The hydrocarbon-air mixture is passed through the catalysts at a concentration of about 1 to about 10 mole percent hydrocarbon at a space velocity of about 100 to 3000 cc/cc/hour and at temperatures between about 350° C. and about 600° C. to provide high maleic anhydride yields.

Maleic anhydride produced by using the catalysts of this invention can be recovered by any number of means well known to those skilled in the art. For example, the maleic anhydride can be recovered by direct condensation or by absorption in suitable media with subsequent separation and purification of the anhydride.

A large number of non-aromatic hydrocarbons having from 4 to 10 carbon atoms can be converted to maleic anhydride using the catalysts of the present invention. It is only necessary that the hydrocarbon contain not less than 4 carbon atoms in a straight chain. As an example, the preferred saturated hydrocarbon is butane, but isobutane which does not contain 4 carbon atoms in a straight chain, is not satisfactory for conversion to maleic anhydride although its presence is not harmful. In addition to butane, other saturated hydrocarbons within the scope of this invention include the pentanes, the hexanes, the heptanes, the octanes, the nonanes, the decanes or mixtures of any of these with or without butane. In addition to the saturated hydrocarbons, unsaturated hydrocarbons can be used. The preferred unsaturated hydrocarbon is butene, but other unsaturated hydrocarbons within the scope of this invention include butadiene, the pentenes, the hexenes, the heptenes, the octenes, the nonenes, the decenes, or mixtures of any of these with or without butene. Cyclic compounds such as cyclopentane or cyclopentene or oxygenated compounds such as furan, dihydrofuran, or even tetrahydrofurfural alcohol are satisfactory. Furthermore, the aforementioned feed stocks are not necessarily pure substances, but can be technical hydrocarbons.

DESCRIPTION OF THE PREFERRED EMBODIMENTS

This invention is illustrated by, but not limited to, the following examples.

EXAMPLE I

This example illustrates the preparation of phosphorus-vanadium-oxygen catalysts for use in a fixed bed reactor, wherein a surfactant is not used.

A phosphorus-vanadium-oxygen catalyst is prepared by slowly adding 133.08 grams of vanadium pentoxide to a mixture of 450 milliliters of water, 84.4 grams of 85% phosphoric acid and 66.04 grams of 99.4% phosphorus acid. The phosphorus to vanadium atom ratio is about 1.05:1. The amount of phosphorous acid is equivalent to about 10% in excess of the phosphorus acid required to convert pentavalent vanadium to tetravalent vanadium. The mixture of vanadium and phosphorus compounds is placed in an autoclave, which is then heated to 100° C. and thereafter sealed. Then, the autoclave containing the vanadium and phosphorus compounds is heated to about 145° C. for about 3 hours. After the autoclave is cooled and opened, large crystals of phosphorus-vanadium-oxygen precursor may be observed in a water suspension.

Excess water from the water suspension is removed by evaporation to form a viscous putty, which is then extruded through a 7/32-inch (0.56 cm) diameter die. The extrudate is then cut into pellets of about 7/32-inch (0.56 cm) lengths. The structured putty is then allowed to air dry, heated to about 90° C. in an oven to evaporate any remaining water, and then calcined at about 350° C. for 8 hours to form a phosphorus-vanadium-oxygen catalyst.

About 50 cc of the catalyst pellets are then charged to a ½-inch (1.26 cm) outside diameter, 6-inch (15.25 cm) long, fixed bed reactor, which gives results comparable to those obtained in a production reactor. When a 2 mole percent butane in air mixture is contacted with the catalyst at a space velocity of about 1450 cc/cc/hour at 417° C., the yield of maleic anhydride is about 49.3 mole percent.

EXAMPLE II

This example illustrates the improved results that are obtained using the process of the present invention.

The catalyst is prepared by the procedure of Example I except that the vanadium pentoxide is added to a mixture of 450 milliliters of water containing 2.9 grams (about 0.4 weight percent) of nonylphenol reacted with about 10 moles ethylene oxide, along with the phosphoric acid and phosphorous acid. When the autoclave is opened, a dispersion is observed of a phosphorus-vanadium-oxygen precursor dispersoid in the water containing the surfactant. When a 2 mole percent butane in air mixture is contacted with the catalyst prepared from the dispersion according to the procedure of Example I at a space velocity of about 1450 cc/cc/hour at 405° C., the yield of maleic anhydride is about 51.2 mole percent.

EXAMPLE III

This example also illustrates the improved results that are obtained when using the process of the present invention.

The procedure of Example I is repeated except that the precursor is calcined at 470° C. for 8 hours. The yield of maleic anhydride at 439° C. is about 44.6 mole percent. However, when the procedure of Example II is repeated except that the precursor is calcined at 470° C. for 8 hours, the yield of maleic anhydride at 404° C. is about 51.5 mole percent.

EXAMPLES IV-VII

These Examples illustrate that improved results are obtained by the process of the present invention when the surfactant is added to the reaction zone even after the vanadium has been reduced to the tetravalent state.

Two batches of catalyst were prepared by the procedure of Example II except that the precursor is calcined at 470° C. for 8 hours. These two batches are identified below as Examples V and VII. Two batches of precursor, identified below as Examples IV and VI, are then prepared according to the procedure of Example I except that 0.4 weight percent nonylphenol reacted with about 10 moles ethylene oxide are added to the precursor after the autoclave is heated to about 145° C. for about 3 hours, and opened. The autoclave with the surfactant and precursor in a water suspension is then heated to about 150° C. for 3 hours more, cooled and opened. The precursor dispersoids were then converted to a catalyst by calcination at 470° C. for 8 hours. The catalyst from each batch is placed in a 1-inch outside diameter, 11-foot long fixed bed reactor, which gives results comparable to those obtained in a production reactor. Maleic anhydride is obtained in the following yields at a space velocity of 1450 cc/cc/hour:

| Example | Butane (mole %) | Reaction Temperature (° C) | Maleic Anhydride Yield (mole %) |
| --- | --- | --- | --- |
| IV | 1.5 | 402 | 55.7 |
| V | 1.5 | 403 | 55.2 |
| VI | 2.0 | 426 | 51.7 |
| VII | 2.0 | 428 | 50.7 |

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. As an example, elements of the Periodic Chart of the Elements in Groups IV through VIII are frequently desirable as catalyst promoters in phosphorus-vanadium-oxygen catalysts and the use of the present invention in treating compositions containing such elements is beneficial. Accordingly, modifications are contemplated which can be made without departing from the spirit of the described invention.

What is claimed is:

1. In a method for preparing a phosphorus-vanadium-oxygen catalyst wherein a pentavalent vanadium compound and a trivalent phosphorus compound are brought together with a chemically inert liquid in a reaction zone under conditions to provide a substantial amount of tetravalent vanadium and to form a phosphorus-vanadium-oxygen catalyst precursor having a phosphorus to vanadium atom ratio between about 0.9:1 and about 2:1, the improvement which comprises adding at least about 0.01 weight percent, based on the total weight of the slurry of a surfactant selected from the group consisting of anionic, nonionic, zwitterionic and amphalytic compounds and mixtures thereof to the reaction zone to form a finely divided phosphorus-vanadium-oxygen catalyst precursor.

2. In a process of claim 1 wherein the amount of surfactant is between about 0.01 weight percent and about 0.5 weight percent, based on the total weight of the slurry.

3. In a process of claim 1 wherein the amount of surfactant is between about 0.05 weight percent and about 0.2 weight percent, based on the weight of the slurry.

4. In a process of claim 1 wherein the phosphorus to vanadium atom ratio is between about 1:1 and about 1.2:1.

5. In a process of claim 1 wherein the surfactant is a nonionic surfactant.

6. In a process of claim 1 wherein the surfactant is nonylphenol reacted with about 9 moles ethylene oxide.

7. In a process of claim 1, wherein said trivalent phosphorus compound is phosphorous acid.

* * * * *